(12) United States Patent
Hong et al.

(10) Patent No.: US 9,057,034 B2
(45) Date of Patent: Jun. 16, 2015

(54) METHOD FOR SYNTHESIZING POLYOXYMETHYLENE DIMETHYL ETHERS

(71) Applicant: Dongfang Hongsheng New Energy Application Technology Research Institute Co., Ltd (CN), Beijing (CN)

(72) Inventors: Zhengpeng Hong, Beijing (CN); Hongyan Shang, Beijing (CN); Chengyue Li, Beijing (CN)

(73) Assignee: DONGFANG HONGSHENG NEW ENERGY APPLICATION TECHNOLOGY RESEARCH INSTITUTE CO., LTD, Beijing (CN)

( * ) Notice: Subject to any disclaimer, the term of this patent is extended or adjusted under 35 U.S.C. 154(b) by 0 days.

(21) Appl. No.: 14/257,722

(22) Filed: Apr. 21, 2014

(65) Prior Publication Data

US 2014/0364651 A1    Dec. 11, 2014

(30) Foreign Application Priority Data

Jun. 9, 2013    (CN) .......................... 2013 1 0230987
Nov. 27, 2013    (CN) .......................... 2013 1 0616042

(51) Int. Cl.
*C10L 1/02*    (2006.01)
*C08G 2/12*    (2006.01)
*C07C 41/56*    (2006.01)

(52) U.S. Cl.
CPC . *C10L 1/02* (2013.01); *C07C 41/56* (2013.01); *C08G 2/12* (2013.01)

(58) Field of Classification Search
None
See application file for complete search history.

(56) References Cited

U.S. PATENT DOCUMENTS

| 7,999,140 B2 * | 8/2011 | Stroefer et al. ............... 568/613 |
| 2007/0260094 A1 | 11/2007 | Schelling et al. |
| 2010/0056830 A1 | 3/2010 | Chen et al. |

FOREIGN PATENT DOCUMENTS

| CL | 102432441 A | 5/2012 |
| CN | 101048357 A | 10/2007 |
| CN | 102295734 B | 10/2012 |
| EP | 1 070 755 A1 | 1/2001 |

OTHER PUBLICATIONS

Database CAPLUS on STN, Acc. No. 2012:1713643, Li et al., CN 102786397 A (Nov. 21, 2012) (abstract).*
Database CAPLUS on STN, Acc. No. 2012:404003, Zhong et al., CN 102372611 A (Mar. 14, 2012) (abstract).*
Database CAPLUS on STN, Acc. No. 2012:2797, Li et al., CN 102295734 A (Dec. 28, 2011) (abstract).*
Jakob Burger, et al. "Poly (oxymethylene) dimethyl ethers as components of tailored diesel fuel: Properties, synthesis and purification concepts," Journal homepage www.elsevier.com/locate/fuel, Fuel 89 (2010) (pp. 3315-3319).
Extended European Search Report for Appl. No. 14171356.0 dated Oct. 29, 2014.

* cited by examiner

*Primary Examiner* — Brian J Davis
(74) *Attorney, Agent, or Firm* — Birch, Stewart, Kolasch & Birch, LLP

(57) ABSTRACT

The present invention relates to the field of chemical engineering and technology, in particular relates to the sub-field of synthesis of high quality alternative liquid fuel for engines from non-petroleum based feedstock, more particularly relates to a method for adjusting, controlling and optimizing the synthetic process of polyoxymethylene dimethyl ethers by utilizing chemical thermodynamic principle. The process of the present invention is achieved by conditions wherein the initial temperature of reaction is controlled at 100-120° C., then the temperature is reduced to 50-70° C. by successive stepwise cooling or programmed cooling, the reaction pressure is controlled at 0.1-4.0 MPa, and the molar ratio of paraformaldehyde or trioxane, metered in formaldehyde units, to methylal in the feedstock is 1.5:1-8:1. In the process, higher overall yield of the target product can be achieved within the same reaction time, and selectivity of products with higher polymerization degree of methoxy groups can be increased.

19 Claims, 1 Drawing Sheet

METHOD FOR SYNTHESIZING POLYOXYMETHYLENE DIMETHYL ETHERS

FIELD OF THE INVENTION

The present invention relates to the field of chemical engineering and technology, in particular relates to the sub-field of synthesis of high quality alternative liquid fuel for engines from non-petroleum based feedstock, more particularly relates to a method for adjusting, controlling and optimizing the synthetic process of polyoxymethylene dimethyl ethers by utilizing chemical thermodynamic principle.

BACKGROUND OF THE INVENTION

Recent investigation shows that, the apparent consumption of diesel fuel in China has already mounted up to about 167 million tons, which leads to frequent occurrence of short supply of diesel fuel (the domestic demand ratio of diesel fuel to petrol is about 2.5:1, but the production ratio thereof is about 2.3:1). Besides the reasons of unreasonable pricing of different types of oil products, and slow price linkage mechanism of domestic petroleum products with international crude oil, the fundamental reason is the constraints of resource shortage. Traditionally, diesel fuel is made from petroleum based feedstock, and the resource endowment of China characterized in relatively "rich in coal, poor in oil, and lack in gas" leads to increasingly prominent contradiction between petroleum supply and relatively fast sustainable development of economics and society. Since China became a net importer of petroleum in 1993, the import volume increases fast and constantly, and the foreign-trade dependence already exceeded 56% after 2011, it has a severe impact on national strategic security of energy.

Furthermore, the worsening crude oil quality leads to continuous scale expansion of domestic catalytic processing of heavy oil and increasing percentage of diesel fuel produced by catalytic processing, which results in gradual decline of the cetane number (CN value) of diesel fuel products and significant increase of noxious substance discharged after combustion, therefore, the urgent problem to be solved is to increase the CN value of diesel fuel.

The tail gas discharged by a diesel engine contains, besides $CO$, $CO_2$ and $NO_x$, a large amount of noxious substance such as unburned hydrocarbon compounds (HC) and particulate matter (PM), which is one of the main sources of PM2.5 contamination in urban air. International Agency for Research on Cancer (IARC) affiliated with World Health Organization (WHO) declared in June, 2012 the decision to elevate the cancer hazard ranking of diesel engine tail gas, from "possibly carcinogenic" classified in 1988 to "definitely carcinogenic". As scientific research advances, now there is enough evidence to prove that diesel engine tail gas is one of the reasons that cause people to suffer from lung cancer. Furthermore, there is also limited evidence indicating that, inhaling diesel engine tail gas is relevant to suffering from bladder cancer. IARC hopes that this reclassification can provide reference for national governments and other decision makers, so as to actuate them to establish more strict discharge standards of diesel engine tail gas. This significant decision undoubtedly puts forward more rigorous requirements of diesel fuel quality.

Reducing the content of noxious substance such as sulfur, nitrogen and aromatic hydrocarbon in fuels by petroleum refining process such as hydrofining is an effective technical route to improve fuel quality, but has very demanding requirements of hydrogenation catalyst and reaction process, with relatively high processing cost. Internationally, many scientific research institutes are carrying out research and development on production technologies of oxygen-containing blending components for petrol and diesel fuel, especially those diesel fuel blending components with high oxygen and high cetane number, and this has recently become a research hotspot in the technical field of new energy.

Polyoxymethylene dimethyl ethers (also known as polymethoxymethylal, dimethyl-polyformal, with the general formula of $CH_3(OCH_2)_nOCH_3$, abbreviated as $DMM_n$, n=8), which is a yellow liquid with a high boiling point, an average cetane number reaching above 76 and increasing dramatically with the increase of its polymerization degree, an average oxygen content of 47%-50%, a flashing point of about 65.5° C., and a boiling point of about 160-280° C., is a clean diesel fuel blending component with a high cetane number. When blending into ordinary diesel by a certain percentage (e.g., 15v %), it can significantly increase oxygen content of diesel fuel products, so as to promote sufficient combustion of diesel fuel and to sharply reduce the discharge of combustion-generated pollutants such as $NO_x$, CO and PM, without the need to make any modification in the fuel supply system of the engine. Furthermore, as polyoxymethylene dimethyl ethers added into ordinary diesel cause the diesel to be diluted, accordingly, the contents of aromatic compounds and sulfides in the diesel fuel products are also reduced.

Synthesis of polyoxymethylene dimethyl ethers may be carried out by processing synthesis gas through a series of steps of methanol, formaldehyde, methylal, and polyformaldehyde etc. The verified coal reserves in China are about 714 billion tons, and developing coal-based methanol industry has huge resource advantages. However, the problem of excessive production capacity of methanol is particularly prominent in recent years. For example, the production capacity of methanol broke through 50 million tons in 2012, but the rate of equipment operation is merely about 50%. Thus the industrial chain of coal chemical industry is in an urgent need to be further extended. Therefore, developing a technologically advanced and economically rational industrial process for synthesizing polyoxymethylene dimethyl ethers based on methanol as upstream feedstock can not only provide a new technology to significantly improve diesel fuel product quality, but also improve the feedstock structure of diesel fuel production, so as to make it more suitable for the resource endowment of domestic fossil energy and enhance the strategic security of domestic supply of liquid fuel for engines.

In the aspect of synthesis of polyoxymethylene dimethyl ethers, a lot of work has been done at home and abroad, regarding research and development of methods for synthesizing polyoxymethylene dimethyl ether products where n=1-10 by using methanol, methylal, lower alcohol, aqueous formaldehyde solution, paraformaldehyde, etc. as feedstock in the presence of acidic catalysts.

In various kinds of feedstock route, more research has been done about the synthesis of polyoxymethylene dimethyl ethers from trioxane or paraformaldehyde together with methylal, including:

U.S. Patent Application US2007/0260094A1 discloses a preparation process of polyoxymethylene dimethyl ether using methylal and trioxane as feedstock in the presence of acidic catalyst. The water contained in the reaction mixture of methylal, trioxane and acidic catalyst should not exceed 1%. Polyoxymethylene dimethyl ether where n=3 and 4 in the reaction product is separated by rectification, and methylal, trioxane and polyoxymethylene dimethyl ethers with polymerization degree of n<3 and some of n>4 can be recycled.

A process of catalytic synthesis of polyoxymethylene dimethyl ethers with polymerization degree of methoxy groups at 2-10, by using methylal and trioxane as feedstock, in the presence of homogeneous or heterogeneous acidic catalysts such as liquid mineral acids, sulfonic acids, heteropolyacids, acidic ion-exchange resin, zeolite, etc., at the pressure of 1-20 bar and the reaction temperature of 50° C.-200° C. and under the condition of strictly limited water content introduced into the system, is disclosed in Chinese Patent Application CN101048357A of BASF Aktiengesellschaft. By optimization, polyoxymethylene dimethyl ethers with polymerization degree of methoxy groups at 3 and 4 can be separated by distillation through three towers.

Tianjin University discloses a process for synthesis of polyoxymethylene dimethyl ethers using methylal and trioxane as feedstock in Chinese Patent Application CN102432441A, which uses cation exchange resin as a catalyst in the fixed bed reactor, under the reaction condition of a reaction temperature of 80° C.-150° C., a reaction pressure of 0.6 MPa-4.0 MPa and a nitrogen atmosphere, mainly obtaining products with n at 3 or 4.

Furthermore, in recent years abroad, Jakob Burger etc. [i.e., Fuel 89 (2010) 3315-3319] synthesized $DMM_n$ using ion-exchange resin as a catalyst and methylal and trioxane as feedstock in a stirred-tank reactor in laboratory by intermittent operation, which focuses on studying the relationship between the reaction equilibrium composition and reaction temperature, feedstock mass ratio. In China, some colleges and universities such as East China University of Technology, Nanjing University, Lanzhou University of Technology, etc. are carrying out some basic and applied basic research in the aspect of chemical thermodynamics, catalyst screening and reaction process.

In conclusion, there has already been lots of research about preparing target product $DMM_n$ using methylal together with paraformaldehyde or trioxane as feedstock, the catalysts involved cover almost all the major types of acidic catalysts, but in the implementation process, no matter what kind of catalyst and reactor are used, the rate of chemical reaction is always very low, and the reaction is generally required to last for hours or even longer, it has become a major challenge which limits large-scale industrialization of this technology.

SUMMARY OF THE INVENTION

The technical problem to be solved by the present invention is, to provide a synthesis process of higher chemical reaction rate, higher one-way yield of target product, high selectivity of target products with higher polymerization degree of methoxy groups.

A method for synthesizing polyoxymethylene dimethyl ethers is provided in the present invention, the synthesis reaction is carried out by using paraformaldehyde or trioxane together with methylal as feedstock in the presence of acidic catalyst, the initial temperature of reaction is controlled at 100-120° C., then the temperature is reduced to 50-70° C. by successive stepwise cooling or programmed cooling, the reaction pressure is controlled at 0.1-4.0 MPa, and the molar ratio of paraformaldehyde or trioxane, metered in formaldehyde units, to methylal in the feedstock is 1.5:1-8:1.

The successive stepwise cooling of the reaction mixture is by means of reducing the temperature by 10-20° C. and then carrying out isothermal reaction for each step, preferably the temperature decreasing amplitude for each step is 10-15° C.

All kinds of acidic catalysts in prior art which can bring about the synthesis of polyoxymethylene dimethyl ethers can be used as the catalyst of the present invention, preferably a strong acidic cation exchange resin, and the strong acidic cation exchange resins currently commercially available can achieve the objective of the present invention.

The amount of the catalyst is equal to 0.3-3.0 wt % of the total amount of the feedstock, and preferably the amount of the catalyst is equal to 2-3 wt % of the total amount of the feedstock.

The molar ratio of paraformaldehyde or trioxane, metered in formaldehyde units, to methylal in the feedstock is 1.5:1-6:1, and preferably 1.5:1-2:1. Preferably the reaction pressure is controlled at 1.0-4 MPa, and more preferably 2-3 MPa.

The reaction time of the synthesis reaction is 2-10 hours, and preferably 4-10 hours.

As an applicable way, the synthesis reaction is carried out in a single-stage tank reactor using batch operation, and successive stepwise cooling in the reaction process is achieved by a programmed temperature control system.

As an alternative way, the synthesis reaction is carried out in multi-stage tank reactors connected in series using continuous operation, and successive stepwise cooling in the continuous reaction process is achieved by controlling temperatures of each respective reactor to be different.

Further, the number of the multi-stage tank reactors connected in series is 2-6.

More preferably, the tank reactor is a slurry bed reactor.

The present invention further discloses polyoxymethylene dimethyl ethers synthesized by the above-mentioned method.

The reaction equation of the process of the present invention is as follow:

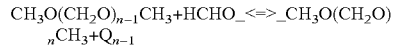

where n is polymerization degree of methoxy groups, and n≥2; $Q_i$ is the quantity of released heat of the $i^{th}$ main reaction, and i=n−1.

Because synthesizing $DMM_n$ using trioxane or paraformaldehyde together with methylal as feedstock is a highly exothermic reversible reaction. It is found in research that the relationship between the equilibrium constant of the reaction and the temperature is significantly dependent on the type of feedstock and polymerization degree of methoxy groups in the reaction product. And from the perspective of structural characteristics of the studied reaction network, the polymerization degree of methoxy groups of the product increases sequentially, and the activity of all kinds of catalysts used so far is generally relatively low, the reaction rate is relatively slow. Similarly in view of the above-mentioned understanding of thermodynamics of the reaction system itself, the reaction network structure and dynamic characteristics, further taking into account that, when using certain feedstock systems, the target product will be synthesized with production of notable amount of water, thus increasing the investment and energy consumption of the post-separation, within the practicable temperature range of the reaction, the equilibrium constant of the synthesis reaction is sensitive to temperature variation, and the level of sensitivity will increase with the increase of polymerization degree of methoxy groups of the product. Based on these understanding of thermodynamic characteristics of the reaction system, it is provided by the present invention to use a specially designed slurry bed reactor system under the conditions of basically eliminating diffusion effect and suitable temperature and pressure to achieve the synthesis reaction.

For a slurry bed reactor using batch operation, for example, a single-stage slurry bed tank reactor using batch operation, successive stepwise cooling or programmed cooling is performed; for slurry bed reactors using continuous operation, including multi-stage slurry bed tank reactors connected in series, as well as tubular slurry bed reactors, tower-type slurry bed reactors and static hybrid-type slurry bed reactors, etc., the spatial distribution of the reaction temperature is optimized, for example, for multi-stage slurry bed tank reactors connected in series using continuous operation, the reaction temperature is reduced stepwise stage-by-stage, so as to repeatedly and duly break through the limitation of thermodynamic equilibrium of the chemical reaction, and to increase the average chemical reaction rate, one-way conversion rate of the feedstock and the overall one-way yield of the target product, at the same time, to improve the selectivity of target product with suitable polymerization degree of methoxy groups, thus strengthening the reaction process.

The aforementioned technical solutions of the present invention have the following advantages, as compared to the prior art:

1. For the feedstock system of paraformaldehyde or trioxane together with methylal and within suitable operating temperature range of the selected catalyst, in consideration of the characteristic that the equilibrium constant of the synthesis reaction is sensitive to temperature variation and the level of sensitivity will increase with the increase of polymerization degree of methoxy groups of the product, the synthesis process by stepwise cooing is designed in the manner of reaction→ being close to chemical equilibrium→ cooling to make the equilibrium shift towards the direction in favor of producing target product→ reacting again, so as to repeatedly and duly break through the limitation of chemical reaction equilibrium, to promote continuously forward reaction, and to increase the average chemical reaction rate, one-way conversion rate of the feedstock and the overall one-way yield of the target product, especially to improve the selectivity of target product with higher polymerization degree of methoxy groups, thus strengthening the reaction process; as compared to the method of maintaining a constant reaction temperature all the time, higher overall yield of the target product can be achieved within the same reaction time, and selectivity of products with higher polymerization degree of methoxy groups can be increased;

2. The technical solution can be achieved with a slurry bed tank reactor using single batch operation, through successive stepwise cooling by a programmed temperature control system, and it also can be achieved by using multi-stage slurry bed tank reactors connected in series using continuous operation, through successive stepwise cooling in the continuous operation system by controlling temperatures of reactors at each stage to be different, which is convenient to carry out.

3. The reaction technical ideas provided by the present invention can easily be extended to other types of continuous-operation reactors in which $DMM_n$ is synthesized by using paraformaldehyde or trioxane together with methylal as feedstock in the presence of acidic catalyst;

4. The method of the present invention can effectively shorten the reaction time and improve one-way yield of the product, and no water is produced in the whole system, so that subsequent purification and refinement processes are relatively simple.

BRIEF DESCRIPTION OF THE DRAWINGS

In order to make the present invention clearly understood more easily, detailed description is further presented below, in accordance with specific embodiments and in conjunction with accompany drawings, wherein.

DETAILED DESCRIPTION OF THE EMBODIMENTS

All kinds of strong acidic cation exchange resin catalysts known in the prior art can be selected and used as the catalyst in the technical solution of the present invention, in the following embodiments. D001 macroporous strong acidic styrene type cation exchange resin and 001×7 strong acidic styrene type cation exchange resin produced by Shanghai Jin Kai Resin Co., Ltd (Shanghai resin factory) are taken as examples to expound the technical effects.

Embodiment 1

Figure 1:
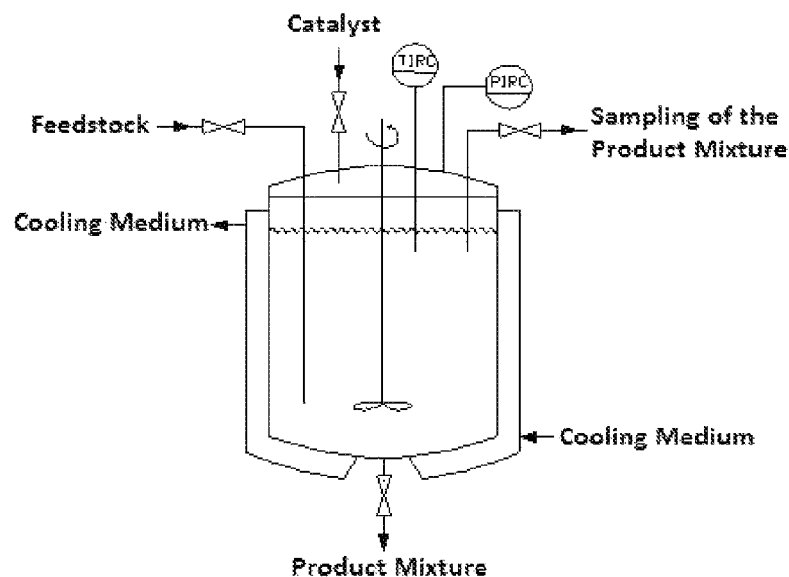
FIG. 1 is a process flow diagram showing the synthesis process of the present invention.

Experimental device of the process flow of this embodiment is shown in FIG. 1. The feedstock of paraformaldehyde and methylal solution is prepared according to a 2:1 molar ratio of paraformaldehyde, metered in formaldehyde units, to methylal, the solution is added into a 0.3 L single-stage stirred tank reactor, and then D001 macroporous strong acidic styrene type cation exchange resin catalyst in the amount of 2 wt % of the overall feedstock is added. The initial pressure of the reaction is controlled at 2.0 MPa, and stirring speed is 250 r/min. And the experiment using stepwise programmed cooling followed by isothermal reaction at each step is carried out in accordance with the following procedures: the reaction mixture is rapidly heated to 100° C., after that the isothermal reaction is carried out for 4 hours; the reaction temperature is rapidly cooled to 90° C. in very short time, then the isothermal reaction is carried out for 2 hours again; the reaction temperature is rapidly cooled to 80° C. in a few minutes, then the isothermal reaction is carried out for 2 hours again; the reaction temperature is rapidly cooled to 70° C. in a few minutes, then the isothermal reaction is carried out for 2 hours again, until the reaction is completed. The sampling is started from when the reaction temperature reaches 100° C. and the timing is started, thereafter samples are taken once per hour for analysis of product composition.

The overall yield of the target product after 10 hours of reaction is 58.74 wt %. It is also found that after 5 hours the concentration of $DMM_8$ in the product has mounted up to about 0.3 wt %.

Embodiment 2

The process flow of this embodiment is the same as that of Embodiment 1. The reaction feedstock and conditions of this embodiment are similar to those of Embodiment 1, and the difference is that the reaction temperature is controlled at 100° C. all the time, after 10 hours the reaction is completed.

The final overall yield of the target product is 51.66 wt %, while $DMM_8$ is not detected throughout the entire reaction.

The Concentration Distribution of Final Products in Embodiment 1 and Embodiment 2 is Shown in the Following Table

| Serial number | $DMM_2$ | $DMM_3$ | $DMM_4$ | $DMM_{5-8}$ | $DMM_{n>8}$ |
|---|---|---|---|---|---|
| Embodiment 1 | 25.45 wt. % | 15.12 wt. % | 8.73 wt. % | 9.44 wt. % | ~0 |
| Embodiment 2 | 22.98 wt. % | 13.72 wt. % | 7.33 wt. % | 7.63 wt. % | ~0 |

As can be seen by analyzing the data in the table, after the same reaction time of 10 hours, the operation scheme of successive stepwise cooling is compared with the isothermal reaction in which the temperature is kept at the initial temperature of the aforementioned successive cooling, and it is found that the concentrations of each kind of the target product of the former are higher than those of the latter, the overall yield of $\Sigma DMM_{2-8}$ is increased by about 7 percentage points, the proportion of $DMM_{5-8}$ in the target product is also higher. It is clearly indicated that successive cooling indeed promotes the equilibrium of the reaction system to shift towards the direction of producing the target product, which not only increases the one-way overall yield of the target product, but also improves the selectivity of target products with higher polymerization degree of methoxy groups, thus strengthening the synthesis reaction.

Embodiment 3

Figure 2:
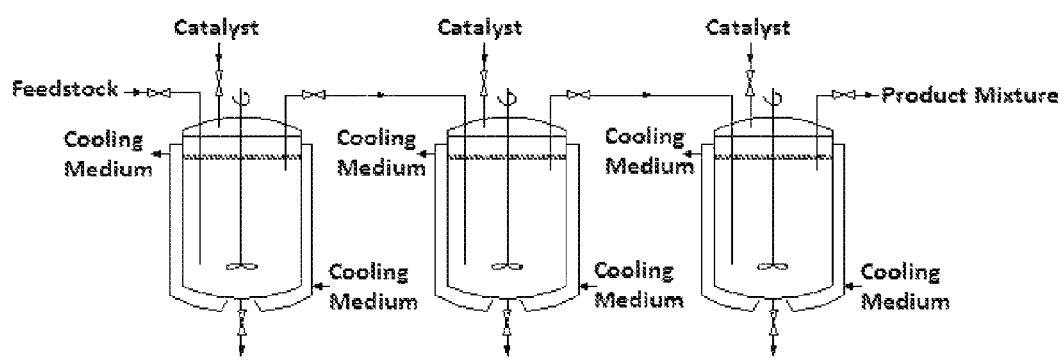
FIG. 2 is another process flow diagram showing the synthesis process of the present invention.

Experimental device of the process flow of this embodiment is shown in FIG. 2. The feedstock solution is prepared according to a 2:1 molar ratio of paraformaldehyde, metered in formaldehyde units, to methylal, the solution is added into a three-stage combination of 5.0 L slurry bed tank reactors connected in series, the temperatures of the first reactor, the second reactor and the third reactor are respectively controlled at 100° C., 80° C. and 60° C., with continuous feeding, and the average reaction time of each tank reactor is kept at about 2 hours. The type and add amount of catalyst and other reaction conditions are all the same as those of Embodiment 1. The operation is carried out continuously until the system is stable and then samples are taken for composition analysis. The final overall yield of the target product is $\Sigma DMM_{2-8}$=57.22 wt %, while $DMM_8$ is detected in the final product.

Embodiment 4

The process flow is as shown in FIG. 2. The feedstock solution is prepared according to a 2:1 molar ratio of paraformaldehyde, metered in formaldehyde units, to methylal, the solution is added into a three-stage combination of 5.0 L slurry bed tank reactors connected in series, the temperatures of the first reactor, the second reactor and the third reactor are all controlled at 100° C., with continuous feeding, and the average reaction time of each tank reactor is kept at about 2 hours until a constant state is reached. The type and add amount of catalyst and other reaction conditions are all the same as those of Embodiment 3. The operation is carried out continuously until the system is stable and then samples are taken for composition analysis. The final overall yield of the target product is $\Sigma DMM_{2-8}$=53.27 wt %, while $DMM_8$ is not detected in the final product.

The Concentration Distribution of Final Products in Embodiment 3 and Embodiment 4 is Shown in the Following Table

| Serial number | $DMM_2$ | $DMM_3$ | $DMM_4$ | $DMM_{5-8}$ | $DMM_{n>8}$ |
|---|---|---|---|---|---|
| Embodiment 3 | 25.02 wt. % | 14.54 wt. % | 8.43 wt. % | 9.23 wt. % | ~0 |
| Embodiment 4 | 23.55 wt. % | 13.71 wt. % | 7.50 wt. % | 8.51 wt. % | ~0 |

As can be seen by analyzing the data in the table, for the three-stage combination of slurry bed tank reactors connected in series using continuous operation, the operation scheme of successive stepwise cooling is compared with the isothermal reaction in which the temperatures of the three reactors are equally kept at 100° C., and after the same reaction time of about 6 hours, it is found that the concentrations of each kind of the target product of the former are higher than those of the latter, the overall yield of $\Sigma DMM_{2-8}$ is increased by about 4 percentage points, the proportion of $DMM_{5-8}$ in the target product is also higher. It is clearly indicated that, for the multi-stage combination of slurry bed tank reactors connected in series using continuous operation, the reaction process of successive cooling provided by the present invention on the basis of thermodynamic equilibrium principle of the reaction system is also effective, it indeed promotes the equilibrium of the reaction system to shift towards the direction of producing the target product, which not only increases the one-way overall yield of the target product, but also improves the selectivity of target products with higher polymerization degree of methoxy groups, thus strengthening the synthesis reaction.

Embodiment 5

Experimental device of the process flow of this embodiment is shown in FIG. 1. The feedstock solution is prepared according to a 1.5:1 molar ratio of trioxane, metered in formaldehyde units, to methylal, the solution is added into a 0.3 L single-stage stirred tank reactor, and then 001×7 strong acidic styrene type cation exchange resin catalyst in the amount of 3 wt % of the overall feedstock is added. The initial pressure of the reaction is controlled at about 2.0 MPa, and stirring speed is 250 r/min. And the experiment using stepwise cooling followed by isothermal reaction at each step is carried out in accordance with the following procedures: the reaction mixture is rapidly heated to 100° C., after that the isothermal reaction is carried out for 1 hour; the reaction temperature is rapidly cooled to 90° C. in very short time, then the isothermal reaction is carried out for 1 hour again; the reaction temperature is rapidly cooled to 80° C. in a few minutes, then the isothermal reaction is carried out for 1 hour, and the reaction is completed after 3 hours in total of reaction. The sampling is started from when the reaction temperature reaches 100° C. and the timing is started, thereafter samples are taken once per hour for analysis of product composition.

The final overall yield of the target product is 47.55 wt % after 3 hours.

Embodiment 6

The process flow of this embodiment is the same as that of Embodiment 1, as shown in FIG. 1. The reaction feedstock and conditions are similar to those of Embodiment 5, and the difference is that the reaction temperature is controlled at 100° C. all the time, after 3 hours the reaction is completed. The final overall yield of the target product is 43.26 wt %.

The Concentration Distribution of Final Products in Embodiment 5 and Embodiment 6 is Shown in the Following Table

| Serial number | $DMM_2$ | $DMM_3$ | $DMM_4$ | $DMM_{5-8}$ | $DMM_{n>8}$ |
|---|---|---|---|---|---|
| Embodiment 5 | 24.88 wt. % | 12.25 wt. % | 5.50 wt. % | 4.92 wt. % | ~0 |
| Embodiment 6 | 24.30 wt. % | 11.27 wt. % | 4.68 wt. % | 3.01 wt. % | ~0 |

As can be seen by analyzing the data in the table, the operation scheme of successive stepwise cooling is compared with the isothermal reaction in which the temperature is kept at the initial temperature of the aforementioned successive cooling, and after the same reaction time of 3 hours, it is found that the concentrations of each kind of the target product of the former are higher than those of the latter, the overall yield of $\Sigma DMM_{2-8}$ is increased by about 4.3 percentage points, the proportion of $DMM_{5-8}$ in the target product is also higher. It is clearly indicated that successive cooling indeed promotes the equilibrium of the reaction system to shift towards the direction of producing the target product, which not only increases the one-way overall yield of the target product, but also improves the selectivity of target products with higher polymerization degree of methoxy groups, thus strengthening the synthesis reaction.

Embodiment 7

Experimental device of the process flow of this embodiment is shown in FIG. 2. The feedstock solution is prepared according to a 1:1 molar ratio of trioxane, metered in formaldehyde units, to methylal, the solution is added into a three-stage combination of 5.0 L slurry bed tank reactors connected in series, the temperatures of the first reactor, the second reactor and the third reactor are respectively controlled at 100° C., 85° C. and 70° C., with continuous feeding, and the average reaction time of each tank reactor is kept at about 1 hour. The type and add amount of catalyst and other reaction conditions are the same as those of Embodiment 5. The operation is carried out continuously until the system is stable and then samples are taken for composition analysis. The final overall yield of the target product is $\Sigma DMM_{2-8}$=46.19 wt %, while $DMM_8$ is detected in the final product.

Embodiment 8

The process flow of this embodiment is shown in FIG. 2. The feedstock solution is prepared according to a 1:1 molar ratio of trioxane, metered in formaldehyde units, to methylal, the solution is added into a three-stage combination of 5.0 L slurry bed tank reactors connected in series, the temperatures of the reactors at each stage are all controlled at 100° C., with continuous feeding, and the average reaction time of each tank reactor is kept at about 1 hour. The type and add amount of catalyst and other reaction conditions are all the same as those of Embodiment 5. The operation is carried out continuously until the system is stable and then samples are taken for composition analysis. The final overall yield of the target product is $\Sigma DMM_{2-8}$=43.07 wt %, while $DMM_8$ is not detected in the final product.

The Concentration Distribution of Final Products in Embodiment 7 and Embodiment 8 is Shown in the Following Table

| Serial number | $DMM_2$ | $DMM_3$ | $DMM_4$ | $DMM_{5-8}$ | $DMM_{n>8}$ |
|---|---|---|---|---|---|
| Embodiment 7 | 24.45 wt. % | 11.77 wt. % | 5.41 wt. % | 4.56 wt. % | ~0 |
| Embodiment 8 | 24.26 wt. % | 11.21 wt. % | 4.60 wt. % | 3.00 wt. % | ~0 |

As can be seen by analyzing the data in the table, for the three-stage combination of slurry bed tank reactors connected in series using continuous operation, the operation scheme of successive stepwise cooling is compared with the isothermal reaction in which the temperatures of the three reactors are equally kept at 100° C., and after the same reaction time of 3 hours, it is found that the concentrations of each kind of the target product of the former are higher than those of the latter, the overall yield of $\Sigma DMM_{2-8}$ is increased by about 3.1 percentage points, the proportion of $DMM_{5-8}$ of the target product is also higher. It is clearly indicated that for the multi-stage combination of slurry bed tank reactors connected in series using continuous operation, the reaction process of successive cooling provided by the present invention on the basis of thermodynamic equilibrium principle of the reaction system is also effective, it indeed promotes the equilibrium of the reaction system to shift towards the direction of producing the target product, which not only increases the one-way overall yield of the target product, but also improves the selectivity of target products with higher polymerization degree of methoxy groups, thus strengthening the synthesis reaction.

The above-mentioned data indicates that, by means of continuous stepwise cooling based on thermodynamic principle in order to break through the chemical equilibrium of the reaction and to promote continuously forward reaction, the present invention is conductive to increase the content of the target product in the whole system and meanwhile to achieve a better distribution of products with higher polymerization degree.

Obviously, the aforementioned embodiments are merely intended for clearly describing the examples, rather than limiting the implementation scope of the invention. For those skilled in the art, various changes and modifications in other different forms can be made on the basis of the aforementioned description. It is unnecessary and impossible to exhaustively list all the implementation ways herein. However, any obvious changes or modifications derived from the aforementioned description are intended to be embraced within the protection scope of the present invention.

The invention claimed is:
1. A method for synthesizing polyoxymethylene dimethyl ethers, comprising performing a synthesis reaction using paraformaldehyde or trioxane together with methylal as feedstock in the presence of an acidic catalyst,
wherein an initial temperature of reaction is controlled at 100-120° C., then the temperature is reduced to 50-70° C. by successive stepwise cooling or programmed cooling, reaction pressure is controlled at 0.1-4.0 MPa, and a molar ratio of paraformaldehyde or trioxane metered in formaldehyde units, to methylal in the feedstock is 1.5:1-8:1.

2. The method for synthesizing polyoxymethylene dimethyl ethers of claim 1, wherein the successive stepwise cooling of the reaction mixture is by means of reducing the temperature by 10-20° C. and then carrying out an isothermal reaction for each step.

3. The method for synthesizing polyoxymethylene dimethyl ethers of claim 1, wherein said catalyst is a strong acidic cation exchange resin.

4. The method for synthesizing polyoxymethylene dimethyl ethers of claim 2, wherein said catalyst is a strong acidic cation exchange resin.

5. The method for synthesizing polyoxymethylene dimethyl ethers of claim 3, wherein an amount of said catalyst is equal to 0.3-3.0 wt % of a total amount of said feedstock.

6. The method for synthesizing polyoxymethylene dimethyl ethers of claim 5, wherein an amount of said catalyst is equal to 2-3 wt % of a total amount of said feedstock.

7. The method for synthesizing polyoxymethylene dimethyl ethers of claim 1, wherein the molar ratio of paraformaldehyde or trioxane, metered in formaldehyde units, to methylal in the feedstock is 1.5:1-6:1.

8. The method for synthesizing polyoxymethylene dimethyl ethers of claim 2, wherein the molar ratio of paraformaldehyde or trioxane, metered in formaldehyde units, to methylal in the feedstock is 1.5:1-6:1.

9. The method for synthesizing polyoxymethylene dimethyl ethers of claim 3, wherein the molar ratio of paraformaldehyde or trioxane, metered in formaldehyde units, to methylal in the feedstock is 1.5:1-6:1.

10. The method for synthesizing polyoxymethylene dimethyl ethers of claim 5, wherein the molar ratio of paraformaldehyde or trioxane, metered in formaldehyde units, to methylal in the feedstock is 1.5:1-6:1.

11. The method for synthesizing polyoxymethylene dimethyl ethers of claim 6, wherein the molar ratio of paraformaldehyde or trioxane, metered in formaldehyde units, to methylal in the feedstock is 1.5:1-6:1.

12. The method for synthesizing polyoxymethylene dimethyl ethers of claim 7, wherein said reaction pressure is controlled at 2-3 MPa.

13. The method for synthesizing polyoxymethylene dimethyl ethers of claim 1, wherein a reaction time of said synthesis reaction is 2-10 hours.

14. The method for synthesizing polyoxymethylene dimethyl ethers of claim 1, wherein said synthesis reaction is carried out in a single-stage tank reactor using batch operation, and successive stepwise cooling in the reaction process is achieved by a programmed temperature control system.

15. The method for synthesizing polyoxymethylene dimethyl ethers of claim 1, wherein said synthesis reaction is carried out in multi-stage tank reactors connected in series using continuous operation, and successive stepwise cooling in the continuous reaction process is achieved by controlling temperatures of each respective reactor to be different.

16. The method for synthesizing polyoxymethylene dimethyl ethers of claim 15, wherein a number of said multi-stage tank reactors connected in series is 2-6.

17. The method for synthesizing polyoxymethylene dimethyl ethers of claim 14, wherein said tank reactor is a slurry bed reactor.

18. The method for synthesizing polyoxymethylene dimethyl ethers of claim 15, wherein said tank reactors are slurry bed reactors.

19. The method for synthesizing polyoxymethylene dimethyl ethers of claim 16, wherein said tank reactors are slurry bed reactors.

* * * * *